United States Patent
Mooney et al.

(10) Patent No.: US 6,383,144 B1
(45) Date of Patent: May 7, 2002

(54) DEVICES AND METHODS FOR MEASURING TEMPERATURE OF A PATIENT

(75) Inventors: Charles R. Mooney, Costa Mesa; Mark Konno, Laguna Beach, both of CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 09/484,555

(22) Filed: Jan. 18, 2000

(51) Int. Cl.$^7$ ................................................ A61B 5/02
(52) U.S. Cl. ........................................ 600/549; 600/435
(58) Field of Search ........................... 600/433–435, 600/504, 505, 526, 549; 604/246, 93.01, 523, 290; 374/100

(56) References Cited

U.S. PATENT DOCUMENTS

| | | | |
|---|---|---|---|
| 3,446,073 A | 5/1969 | Auphan et al. ............. 600/505 |
| 4,632,125 A | * 12/1986 | Webler et al. ............. 600/505 |
| 4,718,423 A | 1/1988 | Willis et al. .............. 600/325 |
| 4,745,928 A | * 5/1988 | Webler et al. ............. 600/505 |
| 4,796,640 A | * 1/1989 | Webler .................... 600/549 |
| 4,817,624 A | 4/1989 | Newbower ................ 600/505 |
| 4,901,734 A | 2/1990 | Griffin et al. ............. 600/505 |
| 4,941,475 A | 7/1990 | Williams et al. ........... 600/505 |
| 5,176,144 A | 1/1993 | Yoshikoshi et al. ........ 600/505 |
| 5,207,227 A | 5/1993 | Powers ................... 600/504 |
| 5,207,228 A | * 5/1993 | Roelandt et al. ........... 600/526 |
| 5,271,410 A | * 12/1993 | Wolzinger et al. .......... 600/505 |
| 5,279,598 A | 1/1994 | Sheaff .................... 604/290 |
| 5,284,138 A | 2/1994 | Kujawski ................. 600/486 |
| 5,373,850 A | * 12/1994 | Kohno et al. .............. 600/505 |
| 5,435,308 A | 7/1995 | Gallup et al. ............. 600/342 |
| 5,509,422 A | 4/1996 | Fukami ................... 600/301 |
| 5,509,424 A | 4/1996 | Al-Ali .................... 600/505 |
| 5,545,137 A | 8/1996 | Rudie et al. ........... 604/102.01 |
| 5,588,438 A | 12/1996 | McKwon et al. ........... 600/505 |
| 5,596,995 A | 1/1997 | Sherman et al. ........... 600/549 |
| 5,611,338 A | 3/1997 | Gallup et al. ............. 600/342 |
| 5,617,870 A | 4/1997 | Hastings et al. ........... 600/505 |
| 5,682,899 A | 11/1997 | Nashef et al. ............. 600/505 |
| 5,688,266 A | 11/1997 | Edwards et al. ............ 606/31 |
| 5,853,409 A | 12/1998 | Swanson et al. ............ 606/31 |
| 5,897,552 A | 4/1999 | Edwards et al. ............ 606/31 |
| 6,162,184 A | * 12/2000 | Swanson et al. ........... 600/549 |

FOREIGN PATENT DOCUMENTS

| | | |
|---|---|---|
| EP | 0226220 A2 | 6/1987 |
| EP | 0266928 A1 | 5/1988 |
| EP | 0417781 A1 | 3/1991 |
| EP | 0440155 B1 | 8/1991 |
| EP | 0522727 A1 | 1/1993 |
| EP | 0235811 B1 | 9/1993 |
| EP | 0599813 A2 | 6/1994 |
| EP | 0357334 B1 | 1/1995 |
| WO | 93/15654 | 8/1993 |

OTHER PUBLICATIONS

510(K) Premarket Notification.

* cited by examiner

Primary Examiner—Kevin Shaver
Assistant Examiner—Charles Marmor, II
(74) Attorney, Agent, or Firm—Lena I. Vinitskaya; Jeffrey Slusher

(57) ABSTRACT

An access device such as a catheter, or introducer, or any combination of the above is provided. Within the access device is at least one lumen, channel or instrument that carries or itself is a thermally active mass, such as infusion fluids, control wires, etc. A temperature sensor such as a thermistor is secured to the access device in order to measure the temperature of a temperature medium, typically blood; in a patient. Various insulating lumens, insulating members and mounting and extrusion configurations are provided by the invention to insulate the temperature sensor thermally from the thermal mass, which might otherwise degrade the accuracy of the temperature measurement. The invention also provides an arrangement whereby the temperature sensor is connected to an external monitor for display of the patient's temperature.

44 Claims, 4 Drawing Sheets

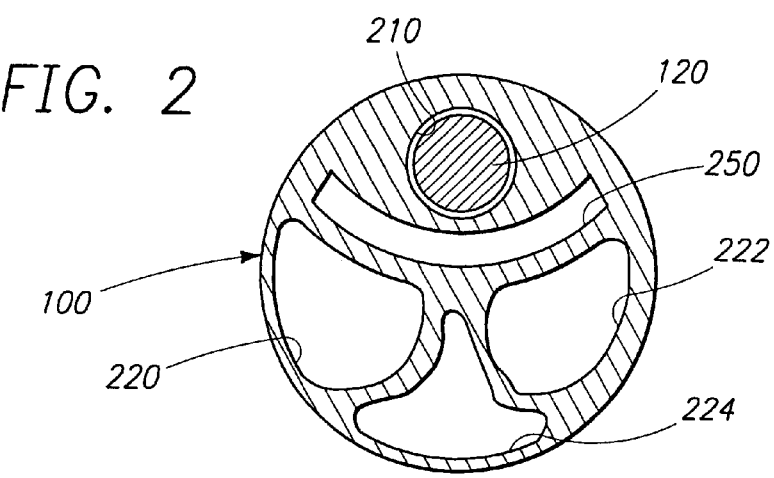
FIG. 2
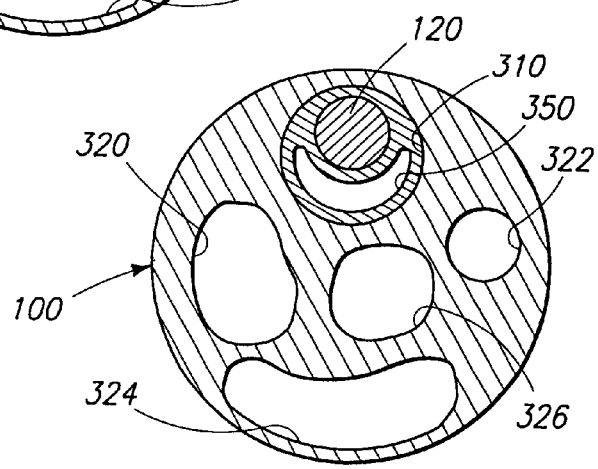
FIG. 3a
FIG. 3b
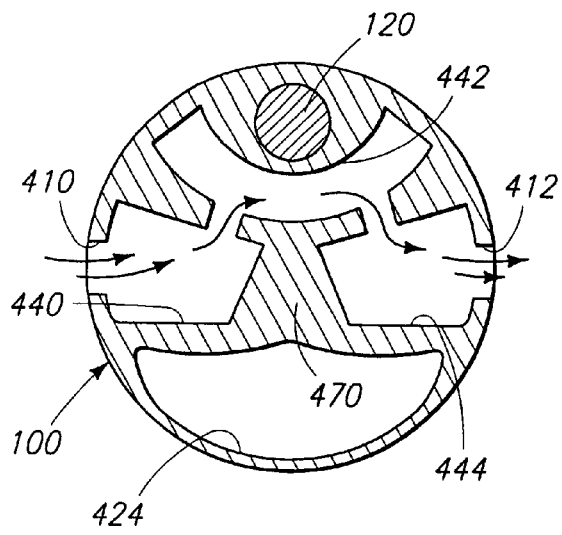
FIG. 4
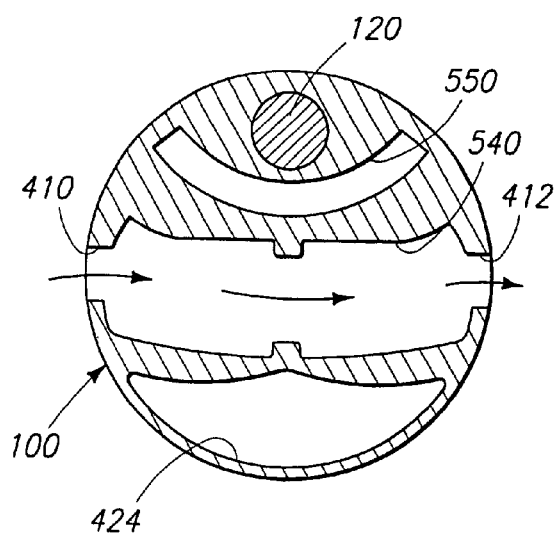
FIG. 5

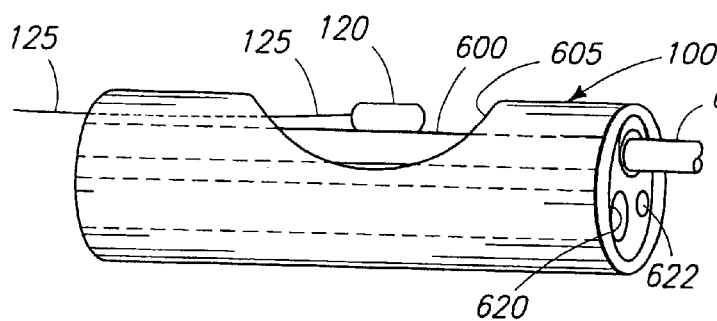 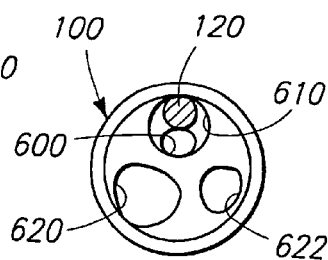
FIG. 6a    FIG. 6b
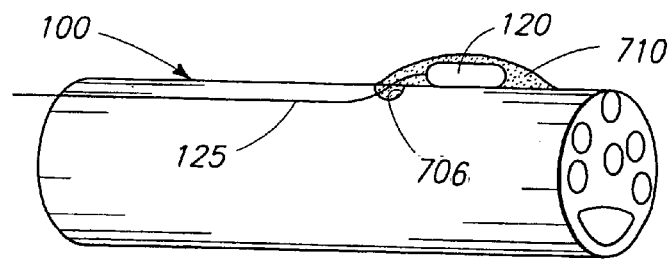 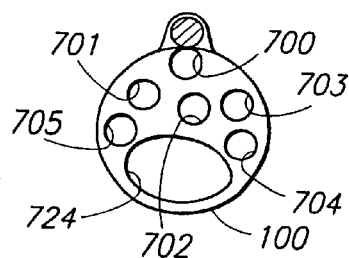
FIG. 7a    FIG. 7b
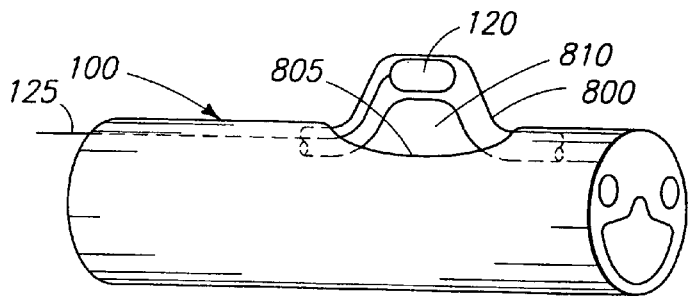 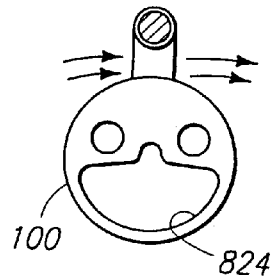
FIG. 8a    FIG. 8b
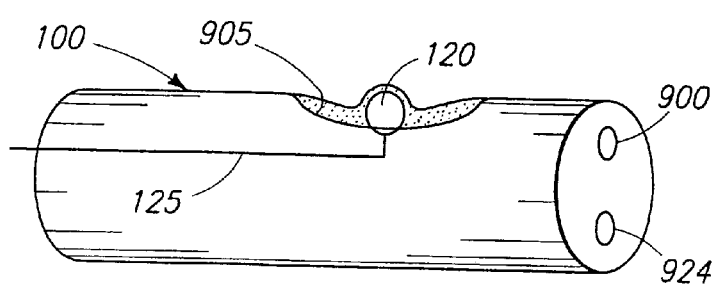
FIG. 9

DEVICES AND METHODS FOR MEASURING TEMPERATURE OF A PATIENT

FIELD OF THE INVENTION

This invention relates to methods and devices for measuring the body temperature of a patient in conjunction with the placement within the patient of an access device, for example, a catheter or introducer.

DESCRIPTION OF THE RELATED ART

The needs to properly treat a patient and to gain as much information as possible about the physiological state of a patient are often at odds with the desire to reduce discomfort to the patient as much as possible. For example, there is frequently a need both to deliver various medications to a patient, and also to monitor the patient's body temperature. Accordingly, catheters are often inserted into the vasculature of a patient to allow delivery of various medications, hydrating fluids, etc., and to measure blood pressure. The patient's body temperature, however, is monitored with a separate device, which is inserted separately.

Conventional devices for measuring temperature include the well-known oral thermometer, rectal, axillary (armpit), and tympanic (ear) thermometers and probes, as well as Foley catheters (bladder temperature), and nasopharyngeal probes (esophagus) probes. Each of these devices suffers from one or more shortcomings. The first disadvantage is obvious to anyone who has ever been the patient: It is uncomfortable enough to have a catheter inserted into one's vein or artery without also having to have a separate device inserted into one's rectum, bladder, ear or nose, or down one's throat.

The second disadvantage has to do with accuracy—taking a patient's temperature by placing a thermometer under her armpit or in her mouth may cause the least discomfort to the patient, but the temperature value this provides is usually less accurate and much more dependent on placement than temperature measurements of blood in a major vessel.

One way to overcome these disadvantages is to include some form of temperature sensor within the inserted catheter itself. This allows for measurement of the blood temperature, which is in most cases much closer to the patient's actual body core temperature. The problem then arises that other elements of the catheter system may have thermal properties that themselves affect the temperature that the sensor senses. This problem arises in the context of thermodilution systems for measuring cardiac flow. U.S. Pat. No. 4,817,624 (Newbower, Apr. 4, 1989), U.S. Pat. No. 5,176,144 (Yoshikoshi, Jan. 5, 1993), and Published European Patent Application 0 357 334 B1 (Inventors: Williams, et al., Mar. 7, 1990) for example, describe such systems. As is well known, in such a thermodilution system, the temperature of the cardiac blood flow is modulated according to a predetermined pattern that is created by the injection of an indicator, which is usually either a series of boluses of a relatively colder fluid, or heat. The downstream response to the temperature modulation is sensed by a thermistor and is used to calculate and estimate blood flow.

In systems such as Newbower's, temperature modulation is accomplished by cooling the blood through precisely dosed boluses of a thermally well-controlled fluid colder than the blood. In Williams, modulated cooling of the blood is accomplished using a heat exchange mechanism that does not require actual injection of any bolus into the blood stream. In systems such as Yoshikoshi's the blood is instead heated locally using a heating element that is mounted near the far (distal) end of a cardiac catheter. As before, a thermistor senses the downstream response profile, whose characteristics are used to calculate cardiac flow.

Such thermodilution systems have certain clinical limitations, since they must deal with several problems specific to this application. First is the problem of retrograde flow: If the thermistor is located proximal to the heater or bolus injection port, then the heated/cooled blood will flow back over the catheter tip. The temperature of the catheter itself, which may contain various other lumens, injectates, control wires, etc. can then affect the temperature profile of the thermally modulated blood and degrade the flow calculations.

To overcome this effect, the injection is replaced by a continuous infusion of indicator in order to obtain a new steady-state baseline; however, this is an undesirable clinical limitation due to the volume-loading the patient. Even when the thermistor is located distal relative to the heater/bolus port, this problem may still arise.

These thermodilution system catheters normally have a distal infusion lumen that passes beneath the thermistor or temperature sensor and exits at the tip of the catheter. Since the flow in such an infusion lumen can severely degrade the accuracy of the temperature sensor measurements, the flow is limited to a maximum amount in order for the blood flow measurement to still be accurate. Of course, such a limitation on infusion lumen flow is also undesirable from the clinical perspective.

An analogous problem of insulation arises in other cardiac devices as well, such as the catheter-based cardiac ablation system described in U.S. Pat. No. 5,688,266 Edwards, et al., Nov. 18, 1997). In Edwards' system, an ablation electrode is used to kill tissue locally using heat, and one or more temperature-sensing elements are used to sense the temperature of the tissue to be ablated and allow precise control of the ablation temperature and time. Isolation, provided primarily by physical separation, is thus required between the electrode and the temperature sensors; otherwise, the sensors will tend to give readings that are too high.

At least one factor limits the use of these known systems in general use for measuring a patient's body temperature: These systems are not arranged to measure the patient's actual, natural body temperature at all, but rather the temperature of blood or some body tissue whose temperature the system itself has deliberately altered.

There are other devices, such as central venous catheters (CVC), peripheral catheters, and other catheter-like instruments such as introducers. As their names imply, such catheters do not require placement into the heart and are consequently used more frequently in different areas of the hospital. Unlike cardiac catheters, which are often more than 100 cm long and require an introducer for insertion, these devices are seldom longer than about 20–30 cm and can be inserted by the Seldinger technique. A CVC, for example, is often placed in a patient's jugular vein and is used for various infusions, for monitoring blood pressure, etc., through a number of lumens within the device.

An instrument such as a CVC often includes several different lumens which may carry a range of fluids (such as medications and other infusions), as well as instruments such as pressure transducers. Each of these fluids and instruments may be at different temperatures, or may have varying thermal properties, or both. Any measurement of temperature using such a catheter would thus risk serious thermal contamination from other portions of the catheter.

There are at present no known devices such as a CVC, peripheral catheter, or introducer that incorporate an arrangement for measuring blood temperature accurately. Therefore, it would be advantageous to be able to accurately measure temperature in conjunction with such access devices as catheters and introducers while eliminating the need to insert a secondary device into the patient in order to measure temperature, as is the current practice. Such devices would also provide a more accurate and less time-consuming body temperature measurement than non- or less invasive devices. This invention provides such an arrangement.

It would also be advantageous to be able to connect a CVC or similar catheter to a standard patient monitor. Not only would this bring the obvious benefit that the patient's temperature could be viewed at a glance along with other monitored parameters, but it would also make the temperature values available for other processing as needed. Many patient monitors, however, use a signal standard that is compatible with large thermistors or temperature sensors and not compatible with the output of miniature temperature sensors used on pulmonary artery catheters. The use of miniature thermistors is desirable because it allows for catheter sizes to be relatively small. One could of course reprogram the monitors, but such a solution to the problem would be costly and complicated, and may not be possible or practical in existing monitors. This invention provides an arrangement that allows a catheter-based temperature sensor to be connected to existing monitors.

An additional issue is that many patients, as their condition improves, do not require continuous monitoring of temperature, and therefore, do not require a dedicated connection between the catheter(s) and the monitor. At present, the dedicated connections limit how many patients the system can monitor, and increases the number of cables and connectors needed. It would be advantageous to free the system to allow monitoring more that one patient. This would, for example, enable nurse or physician to have a quick look at the patient's temperature, possibly enter it into the patient's chart, and then move on to other tasks or patients. It would therefore be beneficial to have an arrangement that provides this flexibility and simplicity. This invention does this as well.

SUMMARY OF THE INVENTION

In general, the invention provides an access device, such as a catheter, an introducer, or combination of catheters, introducers, probes and the like, that allows more accurate sensing of body temperature, for example, of a temperature medium such as blood, by insulating a temperature sensor from thermal contamination caused by a thermal mass, such as an infusion fluid or an instrument, introduced in portions of the access device. In the preferred embodiment of the invention the access device is a central venous device that includes a temperature sensor such as a thermistor, a thermocouple, etc.

The access device is insertable into the patient at a location of the temperature medium, and the access device includes at least one thermal mass other than the temperature medium. The access device supports the temperature sensor and includes at least one insulating structure insulating the temperature sensor from the thermal mass.

In certain embodiments of the invention, each thermal mass is located within a thermal lumen within the access device. The temperature sensor may be mounted externally to an outer surface of the access device, or within a sensor lumen of the access device. The insulating structure preferably extends between the temperature sensor and each thermal lumen.

The temperature sensor may also be mounted in or on a carrier. The insulating structure is then preferably formed as a barrier within the carrier and the carrier is held in one of the lumens of the access device with the barrier extending between the temperature sensor and the thermal lumen. The carrier may be removably insertable in the lumen of the access device.

In other embodiments of the invention, a pair of ports is formed in an outer wall of the access device and a flow channel is formed within the access device and extends between the pair of ports. The temperature medium, such as blood, then occupies the flow channel. The flow channel is located between the temperature sensor and the thermal lumen, or between the insulating structure and the thermal lumen, and thereby not only increases thermal contact between the temperature sensor and the temperature medium, but it also thermally isolates the temperature sensor further from the thermal lumen. The flow channel may thus itself form the insulating structure.

In another embodiment of the invention, the access device has an opening in an outer wall and the temperature sensor, when in a deployed position, extends into the opening. This increases thermal contact between the temperature sensor and the temperature medium and further insulates the temperature sensor from the thermal mass. If the temperature sensor is mounted on a carrier, then ends of the carrier may be secured within the access device. The carrier is then positioned between the temperature sensor and each thermal lumen, thereby forming the insulating structure.

The temperature sensor may alternatively be mounted within the carrier, which then protrudes as a loop out through the opening in the outer wall of the access device. The ends of the carrier are then preferably secured within the access device. In this embodiment, the insulating structure comprises a flow channel for the temperature medium, which is formed between the carrier and the access device at the position of the opening, and thus between the temperature sensor and the thermal mass. One advantage of this embodiment is that the temperature sensor is exposed substantially over its entire outer circumference to the temperature medium, via only the carrier.

Alternatively, the temperature sensor may be a right-angle thermistor mounted to extend out of the opening mainly perpendicular to a central axis of the access device.

In another embodiment of the invention, the temperature sensor is adhesively attached to the access device. The adhesive may be dissolvable at body temperature, so that the temperature sensor separates from contact with the access device when in position within the patient.

The access device may include a plurality of lumens, whereby the temperature sensor is mounted within a recess in an insulating member. The insulating member, together with the temperature sensor, are then mounted within one of the lumens of the access device so that the insulating member extends between the temperature sensor and the thermal lumen.

In another embodiment of the invention, the insulating structure includes an insulating material that is co-extruded with the access device and surrounds either at least a portion of each thermal lumen, or the temperature sensor itself.

In yet another embodiment of the invention, the access device has a lumen and a sensor port and the temperature sensor is mounted on a distal tip of a separate device, for example, a probe. The probe is insertable into the lumen of the access device so that the temperature sensor extends through the sensor port.

The insulating structure may also comprises a distal tip of the access device itself. The tip is then preferably formed from an insulating material as a separate member, and the temperature sensor is mounted within the distal tip. Alternatively, the distal tip of the access device may be provided with a lengthwise extending slit. The temperature sensor is then mounted on a first side of the distal tip and at least one thermal lumen carrying the thermal mass extends through a second side of the distal tip. The distal tip, in a deployed position, then separates along the slit, with the first and second sides of the tip being located on either side of the slit.

In another embodiment of the invention, the insulating structure is a lumen or a chamber in the access device that is expandable to increase the distance between the temperature sensor and the thermal mass.

The access device according to the invention is preferably included as a sensing member in a more general system for monitoring the body temperature of a patient. In this system, the access device is insertable into the patient and is connected to a temperature monitor that converts a sensor output signal of the access device into a patient temperature signal and for displaying the patient temperature signal. A connector is then provided to connect the temperature sensor with the temperature monitor.

The system according to the invention preferably further includes an adapter in the temperature monitor. The adapter converts the sensor output signal into a predetermined display format. The temperature monitor may also be provided with a display and a power supply, in which case the entire monitoring system may be implemented as a hand-held, self-contained unit that is portable between different patients.

The invention also encompasses a method for measuring the body temperature of the patient. The main steps of the method according to the invention involve supporting the temperature sensor on the access device; inserting the access device into a blood vessel; introducing at least one thermal mass into the access device; and insulating the temperature sensor from the thermal mass. In the preferred method according to the invention, the thermal mass is introduced via a thermal lumen located within the access device. One then mounts the temperature sensor in a sensor lumen within the access device and forms at least one thermally insulating structure between the temperature sensor and the thermal lumen. In some embodiments, to provide the thermally insulating structure, one may introduce a thermally insulating material into a lumen within the access device.

The invention also comprises a method for manufacturing the access device. In the preferred embodiment, this method comprises extruding the access device, forming a thermal lumen through which a thermal mass is introduced, forming a sensor lumen through which a temperature sensor is introduced, and forming an insulating structure separating the sensor lumen from the thermal mass. In manufacturing the access device, the temperature sensor may be mounted in the sensor lumen at a distal end of the access device. A signal wire is then drawn from the temperature sensor to an external patient monitor.

BRIEF DESCRIPTION OF THE DRAWINGS

FIG. 2 illustrates another example of an embodiment of the invention in which a temperature sensor is located within a lumen of a catheter but is thermally insulated from other lumens by an insulating gap.

FIG. 3a illustrates a temperature sensor that is provided within a dedicated tubular member that also includes a built-in insulating lumen.

FIG. 3b shows the lumen of FIG. 3a in place in the catheter.

FIGS. 4 and 5 show embodiments of the invention in which blood is allowed to flow past the temperature sensor in place in the catheter, with and without an insulating gap being provided between the temperature sensor and catheter lumens.

FIGS. 6a and 6b are side and end views, respectively, of another examplary embodiment of the invention in which the temperature sensor is mounted on an Insulating member, whereby both are inserted into the same catheter lumen.

FIGS. 7a and 7b are side and end views, respectively, of an embodiment of the invention in which the temperature sensor is mounted on the outer surface of the catheter.

FIGS. 8a and 8b are side and end views, respectively, of another embodiment of the invention in which the temperature sensor is mounted to extend out from the outer surface of the catheter, with a blood flow channel located between the temperature sensor and the outer surface.

FIG. 9 illustrates an embodiment of the invention in which the temperature sensor is a right-angle thermistor extending through an opening in the outer surface of the catheter to provide surface contact between the temperature sensor and the blood.

DETAILED DESCRIPTION

Figure 1:
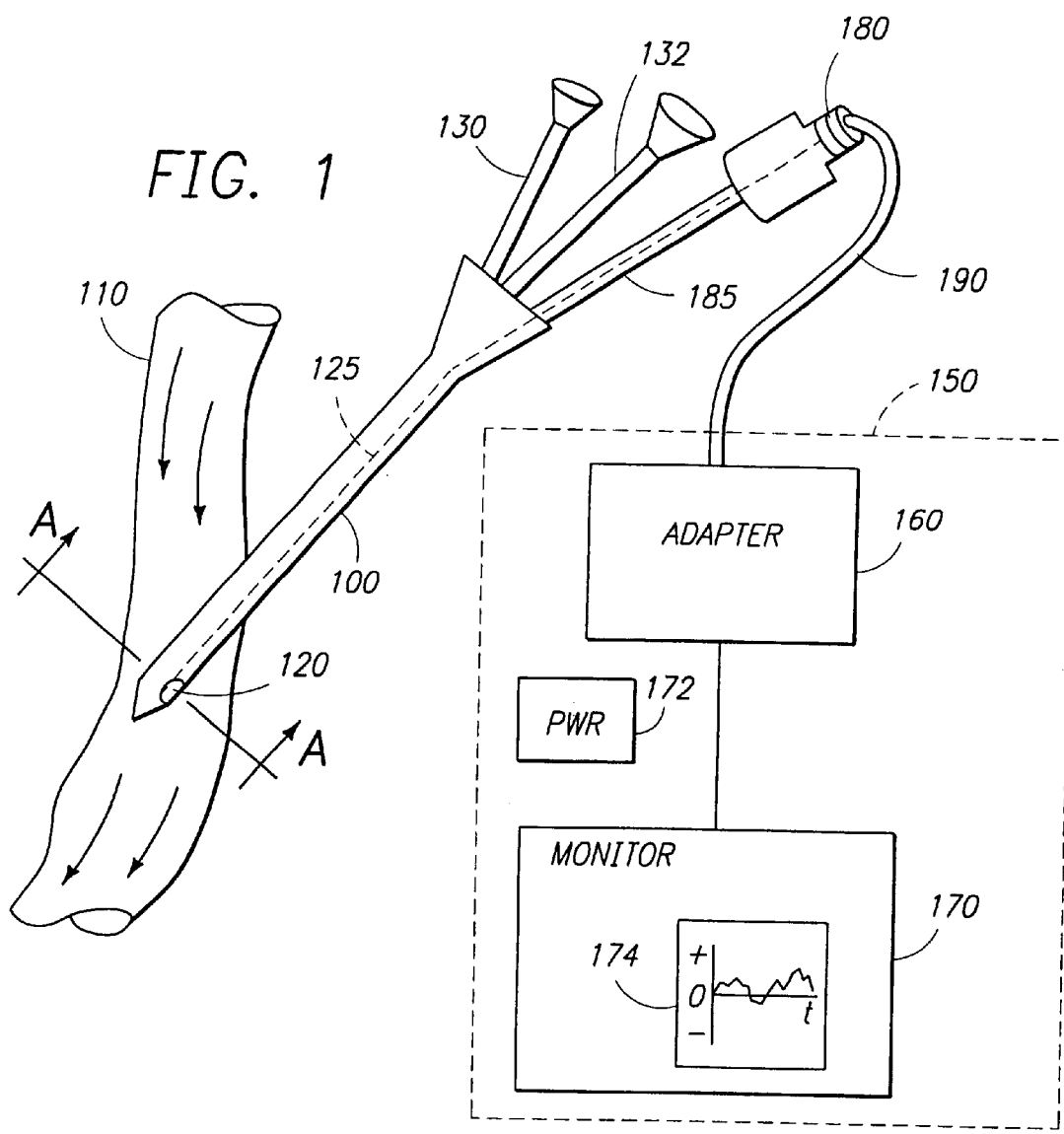
FIG. 1 illustrates one example of an access device according to the invention, such as a CVC catheter, that is inserted into a patient's vein for measuring temperature.

In broadest terms, this invention provides an arrangement or a device in which a temperature sensor is used with an access device, preferably a vascular access device, for insertion into the body of a patient. This invention also provides various insulating structures that reduce thermal contamination of the temperature sensor from other portions of the interior of the access device. The temperature sensor is designed to sense some temperature medium within the patient's body, for example, blood.

One example of the preferred access device of this invention is a central venous catheter (CVC), but it could be some other instrument that also carries or includes fluids or other devices—cumulatively "thermal masses"—that could affect the temperature at the temperature sensor. Examples of other access devices include peripheral catheters, introducers, obturators, and probes. In fact, the term "access device" also contemplates any combination of these devices, such as a combination of one or more introducers, catheters and probes. For example, a catheter is often inserted within an introducer, and either or both could be arranged according to suitable embodiments of the invention to improve the accuracy of temperature measurements.

In the context of this invention, a thermal mass is any substance or structure carried within the access device that has or could have a temperature and heat capacity such that heat flow into or out of the mass could significantly affect the sensed temperature. Here, "significantly" means so much that the temperature measurement would not be acceptably accurate for clinical use.

As used in this invention an "insulating structure" is any structure that insulates the temperature sensor from a thermal mass. As is described and illustrated below, insulating structures used in the invention, include, but are not limited to, a device lumen or any portion of a device lumen, a channel, a gap, a chamber or just an area provided immediately surrounding the temperature sensor. An insulating structure may also include an insulating material, for example, a ceramic, or a separate device such as a probe that is inserted into or through the access device.

The examples of suitable access devices described below are preferably made of biocompatible polymer materials, since in most cases they will be inserted at least partially into a patient. Polyurethane is the most common material, since it meets all normal requirements for thermal and mechanical stability when in a patient; PVC and Teflon are also acceptable, as well as other conventional materials. The access devices for use with this invention may, moreover, be made of an anti-microbial material or may be covered with material or coating having anti-microbial or thromboresistant properties.

The temperature sensor used in this invention may be any conventional device. The most easily implemented sensor is a thermistor, which is small, widely available and relatively easy to calibrate. Other temperature sensors may, however, also be used. Alternatives include conventional thermocouples and fiber optic temperature sensors. The only requirement is that the sensor should predictably change a measurable physical property, such as its electrical resistance or optical spectrum, in response to changes in temperature, and this change should be detectible externally via an electrical or optical conductor in such a way that temperature can be converted to an electrical signal. These devices, and the way in which their signals are conditioned for further processing are well known.

In the following discussion of the various exemplifying embodiments of the invention, it is assumed merely by way of example that the access device is a CVC, that the temperature sensor is a thermistor, that the catheter is inserted into a body vessel, such as a vein, and that the temperature medium whose temperature is to be determined is blood. The invention will work just as well with other access devices and sensors, insertion points, and temperature media, as will be obvious to those skilled in the art.

FIG. 1 illustrates the general structure of the invention. A catheter 100 is inserted into a patient's vein 110 in the conventional manner. Arrows within the vein 110 indicate flowing blood. A thermistor 120 is positioned at the distal end of the catheter, which includes lumens, channels or tubes through which fluids can be infused into the patient, or which hold other instruments. Two conventional infusion connectors 130, 132, are shown inserted into respective lumens in the catheter. The number of lumens and connectors will of course depend on the particular catheter used and the application. The invention will work with any number of lumens or internal channels in the catheter.

A conductor (shown as the dashed line 125), which forms a signal wire, connects the thermistor electrically (or optically, depending on the type of temperature sensor used) with external conditioning, processing and display circuitry 150. In FIG. 1, this exemplary circuitry is shown as including a signal adapter 160 and a patient monitor 170, with a conventional electrical coupler 180 and a guide tube 185 connecting the thermistor signal wire 125 to the external circuitry 150. A conventional power supply 172 is also included, as is a temperature display 174, which may be either a separate display device or simply a portion of an existing monitor display. These features, some of which are optional or can vary depending on the embodiment, are described below in greater detail. Any conventional devices and circuits may be used to communicate the thermistor's 120 output signal to external monitors or displays.

FIG. 1 also shows a section line A—A. The description of various embodiments of the catheter according to the invention is illustrated by cross-sectional drawings. Line A—A is the reference line for these cross-sectional views.

FIG. 2 illustrates one exemplifying embodiment of the invention. In this embodiment, the thermistor 120 is located within a dedicated opening or lumen 210 within the catheter 100. In this figure, the thermistor lumen 210 is shown as being mainly circular. This is not necessary; any appropriate and desired lumen shape may be used. A circular or at least rounded lumen cross section will in most cases be preferable, however, since standard thermistors frequently are provided as glass-encapsulated beads with a mainly round cross section. Three other lumens 220, 222, 224 are also illustrated (however, any number of lumens may be included).

Assume now that one or more of the lumens 220, 222, 224 carries some fluid (or contains some instrument) with a thermal mass and temperature that could affect the temperature measured by the thermistor 120. For example, an infusion fluid might be administered through the lumen 220. If the temperature of the fluid is above or below that of the patient's blood, then it could influence the temperature measurement because of the thermal conductivity of the catheter material between the thermistor and the fluid. An additional insulating structure, such as a lumen or gap 250 is therefore preferably extruded in the catheter so as to extend, for example, laterally between the thermistor and all the other lumens 220, 222, 224.

The insulating lumen (gap) 250 is preferably as wide and thick as possible to maximize the degree of thermal insulation of the thermistor, given the minimum permissible material thickness required to maintain stability of the catheter and lumen walls, as well as the maximum outer diameter of the device. The minimum distance between the thermistor lumen 210 and the outer surface of the catheter 100 is, however, preferably as small as possible to ensure the best thermal contact between the thermistor and the surrounding blood.

The insulating structure, such as the lumen or gap 250 of FIG. 2 is preferably filled with air, or with some other conventional gas, ceramic pellets, a conventional high-impedance gel, etc., to additionally increase its thermal impedance. The insulating material may also be a strip or layer or similar separate piece of an insulating material that is inserted into the lumen 250. This insulating material may optionally be bonded to the catheter in any known way. The most distal end of the insulating lumen is preferably sealed to prevent inflow of blood and outflow of the thermally insulating gas or other insulating material.

In FIG. 2, only one insulating lumen is shown. This is by way of example only. More than one gap may be created, space permitting, to extend between the thermistor and the other lumens to further increase the thermal isolation of the thermistor. Also, the insulating lumen may be of any length—it may extend through the full length of the access device or any appropriate portion of its length. For example, a portion of the lumen 250 may be used as an infusion or device lumen for introduction of medications or guidewires. A plug may be placed somewhere along the length of such lumen to block off the remainder of the infusion/device lumen so that the remaining portion will act as an insulating structure. The location of the plug must be selected such that the blocked off portion of the infusion/device lumen will be adjacent to the location of the temperature sensor. It will be necessary to provide a side port prior to the location of the plug to allow the infusion/device to exit the access device.

The lumen(s) 250 also does not need to be shaped as a generally laterally extending slit, as shown in FIG. 2, although this typically maximizes the isolation of the thermistor from the other lumens. Instead, lumen 250 may be shaped as half-moon or be concentric with the thermistor lumen, or otherwise extruded so as to surround the thermistor lumen 210. Also, the gap could be created by several mainly cylindrical or otherwise curved lumens spread out between the thermistor and the other lumens 220, 222, 224.

In yet another variation of the insulating lumen 250 it—that is, the catheter material around and defining it—is made elastic enough that the lumen 250 is inflatable after the catheter is inserted into the patient. For example, the lumen 250 could be formed to have flexible webs. Once the catheter is inserted, any suitable pressurizing material, such as air, an inert gas, foam, or some other known thermal resistance material could be pumped into the lumen 250, causing its cross-sectional area to expand and increase the gap or distance between the thermistor and thermal masses. The embodiment facilitates easy insertion of the device by keeping its outer diameter small, since the insulating lumen or structure is expanded only after the device is in place.

The lumens 220, 222, 224 may be used for any conventional purpose. Any or all of them may, for example, carry fluids, or act as channels for guiding other instruments such probes, pressure transducers, etc. Of course, they need not all have the same function—one lumen might be carrying an infusion fluid while another is a channel for an instrument.

FIGS. 3a and 3b illustrate an embodiment of the invention in which the thermistor 120 and a thermally insulating lumen/gap 350 are provided in a separate mainly tubular member 300 which may be inserted into an existing lumen 310 or channel within the catheter 100. The tubular member 300 is preferably made of the same—or at least same type of material as the catheter itself, that is, a thermally stable, biocompatible polymer such as polyurethane. This material requirement is not as strict as for the catheter itself, however, since the tubular member is mounted within the catheter. The gap 350, which may be filled with further insulating materials as described above for the lumen 250, is then oriented within the lumen 310 so as to extend between the thermistor and other lumens 320, 322, 324, 326 within the catheter. In order to provide proper orientation of the tubular member within the lumen 310, a key (not shown) such as a rod shaped to conform to the gap 350 could be provided, if needed. The user can then first insert the member 300, with the thermistor, into the lumen 310 and then insert the key into the proximal end of the gap 350 and turn the member 300 into proper alignment.

FIGS. 4 and 5 illustrate embodiments of the invention in which blood itself is channeled between the thermistor 120 and one or more other lumens 424, which may be carrying sources of thermal "noise" such as infusion fluids. In these embodiments, ports 410, 412 are formed in mainly diametrically opposing portions of the outer wall of the catheter 100 and a channel is formed (as part of the normal extrusion between the two ports). The ports 410, 412 may be arranged anywhere along the circumference of the catheter wall—not just diametrically opposing—as long as blood can flow between the temperature sensor and the thermal masses. In FIG. 4, the channel has three chambers—two outer chambers 440, 444 and an intermediate chamber 442—through which blood can flow (indicated by arrows passing though the channel). Note that the ports 410, 412 need be formed only in the region of the thermistor 120, and can thus be simple holes or slits cut in the catheter wall. The channel may be formed as a small chamber or it may extend over any length of the catheter as a result needed to simplify the extrusion. Note that a CVC or peripheral catheter, unlike a cardiac catheter, is typically no more than about 30 cm long, so it will in general not be a problem to let the channel extend as far as the other lumen(s) 424.

In the embodiment of the invention shown in FIG. 4, the blood is directed to a region—the intermediate chamber 442—immediately adjacent to (that is, extending just under, viewed as in FIG. 4) the thermistor 120; the maximum distance separating the thermistor from blood whose temperature is to be measured both above and below can be made as little as the minimum structurally allowable thickness of the catheter material. The blood thus not only helps isolate the thermistor from the lumen(s) 424, but it also better contacts the thermistor thermally, since it does so from two sides instead of just one. A central ridge or tab 470 may be extruded to extend between the two outer chambers 440, 444 and from the lumen 424 toward the thermistor, in order not only to direct the inflowing blood past the thermistor, but also to reduce the amount of blood within the catheter while still allowing for an insulating layer of blood to flow between the thermistor and the lumen(s) 424. The ridge is, however, not necessary to this embodiment of the invention.

In the embodiment of the invention illustrated in FIG. 5, the chambers 440, 444 and 442 and the ridge 470 (FIG. 4) have been eliminated. Instead, the intermediate chamber 442 is sealed off from the blood flow and thus forms an insulating gap or lumen 550, similar to the lumen/gap 250 in FIG. 2. In this embodiment, the blood flowing through the single channel 540 serves mainly to isolate the thermistor thermally from the lumen(s) 424. The lumen/gap 550 provides an additional insulating barrier, although it is not required, especially if the flow of blood through the channel is fast enough to preclude significant heat transfer to or from the thermal mass from which the channel separates the thermistor. Note that another advantage of the embodiment shown in FIG. 5 is that the blood in the channel 540 also tends to bring the temperature within the gap 550 to blood temperature and thus further insulates the thermal mass.

In the embodiments of the invention shown in both FIGS. 4 and 5, the channel 540 may be a limited chamber located near the thermistor itself, or it may be a lumen passing through any portion of the length of the access device. In either case, the channel 540 itself (with passing blood) serves as an insulating structure.

FIGS. 6a and 6b are a partially cut-away, side view and an end view, respectively, of another embodiment of the invention in which the thermistor 120 is mounted on a carrier 600, which is preferably made of a biocompatible material and also provides improved thermal insulation. It may be made, for example, of plastic, metal or ceramic. The thermistor may be mounted securely onto the carrier using any conventional material such as a standard adhesive such as potting compound or a non-toxic, moisture-proof, thermally stable glue.

In this embodiment a port is formed as a cut-away opening 605 in the outer wall of the catheter 100. The thermistor is then positioned so as to lie within the opening in the catheter and thus be exposed directly to the blood over most of its surface are, without any portion of the catheter in between. The thermistor's signal wire 125 is also shown in FIG. 6a.

The thermistor 120 and its carrier 600 may be inserted into an existing or dedicated lumen 610 in the catheter so that the carrier extends between the thermistor and other lumens 620, 622 or thermal noise sources in the catheter. Note that the opening 605 preferably extends into the lumen 610 to ensure maximum direct contact between the thermistor and the surrounding blood.

The thermistor and carrier 600 may be inserted into the catheter with the thermistor in position in the opening 605 before the catheter is placed within the patient. Alternatively, before insertion, and assuming the carrier is made of a sufficiently flexible material, the thermistor and the far, distal end of the carrier 600 could be allowed to stick out of the opening 605, preferably bent back along the catheter wall and pointing away from the direction of insertion. Once thermistor catheter is placed in the patient, the physician could then pull on the proximal end of the carrier until the thermistor is pulled into place in the opening 605. The distal end of the carrier can then be made short, extending only a short distance from the thermistor, so that only its proximal end would be within the catheter. The carrier, which may be tubular, then forms an insulating gap beneath the thermistor, similar to the gaps 250, 350 and 550 in previous embodiments described above.

FIGS. 7a and 7b are a partially cut-away, side view and an end view, respectively, of an embodiment of the invention in which the thermistor 120 is mounted on the outer wall of the catheter 100 itself. In order to avoid having the thermistor's signal wire or fiber 125 running along the outer surface of the catheter to the exterior, it is pre-threaded into the catheter 100 through a small hole 706 made in the catheter wall, preferably just behind (proximal relative to) the thermistor 120. The thermistor may be mounted securely onto the catheter using any conventional method or material such as a standard potting compound 710, or a non-toxic, moisture-proof, thermally stable glue, or a liquefied solution of the catheter material that would solvent bond to the catheter tubing. The potting compound should be spread to cover the hole 706 and at least most of the thermistor, but not so thickly over the thermistor as to interfere with its ability to quickly and accurately respond to temperature changes. In order to reduce the maximum diameter of the catheter and thereby make insertion easier, an indentation could be made in the outer wall of the catheter. The thermistor can then be mounted on the catheter by potting it securely in the indentation (not shown).

In the embodiment of the invention shown in FIGS. 7a and 7b, it would also be possible to mount the temperature sensor using a non-toxic potting material (or other adhesive) that dissolves when exposed to the blood. Once the catheter is in place, the potting material would therefore dissolve. This would expose the temperature sensor directly to the blood and thus allow for even more accurate temperature measurements. Moreover, the temperature sensor will then tend to separate and move away from the outer wall of the catheter, thereby further insulating it from any thermal masses within the catheter.

This "deployment" action may also be arranged by providing the signal wire with an elbow joint made of a memory metal that is straight (extending in the direction of the catheter) during inserting but that is bent in the relaxed state—when the potting compound dissolves, the joint would relax and bend, thus moving the temperature sensor out from the catheter wall. If it is not practical to form this memory elbow joint in the sensor's signal wire itself, then a piece of memory metal could be attached to the wire where the elbow joint is needed. The sensor could then also be potted within an indentation such as in FIG. 6a, so that the catheter could have an outer surface free of protrusions.

As FIGS. 7a and 7b show, several lumens 700–705 or tubular members are preferably included within the catheter in order to provide insulating gaps between the externally mounted thermistor 120 and the lumen(s) that carry infusions. A single lumen/gap such as the lumen 250 shown and described in reference to FIG. 2, or a blood channel similar to the channels shown in FIGS. 4 and 5 may be included instead of or in addition to the lumens 700–705 to further insulate the thermistor thermally from the lumen 724.

FIGS. 8a and 8b are a partially cut-away, side view and an end view, respectively, of an embodiment of the invention in which the thermistor 120 is mounted within a short tubular member 800 that protrudes out through an opening 805 made in the outer wall of the catheter 100. The two ends of the tubular member 800 are secured within the catheter using any known technique. A channel 810 is thereby formed between the "loop" of the tubular member 800 and the catheter. Blood will therefore be able to flow substantially completely around the thermistor 120 and will also isolate the thermistor thermally from any interior lumen(s) 824 within the catheter. During insertion of the catheter, the member 800 will preferably lie flat, that is, mostly straight, within the catheter.

Once the catheter is in place, the physician could then insert the thermistor, for example by pushing it in with a wire, and could then push the thermistor and loop of the member 800 out through the opening 805 to deploy the temperature sensor, that is, the thermistor. One way to do this would be to insert a separate instrument that has a bend on it into, for example, a lumen in which the member 800 lies (or simply the interior of the catheter). Twisting the instrument with the bend under the thermistor would then push it out through the opening 805. Alternatively, if the far distal end of the tubular member 800 is fixed in the catheter, and if the member 800 is not too flexible, then it would push out through the opening by the physician pushing the proximal end inward.

FIG. 9 illustrates an embodiment of the invention in which the thermistor 120 is a right-angle device, that is, there is a substantially right-angle bend in the rod or wire that connects it to its signal wire 125. Of course, angles of bend other than 900 may also be used—the proper angle of bend will depend on the particular implementation and may be determined using known methods. This right-angle thermistor 120 is then potted securely in an opening 905, similar to the openings 605 and 805, formed in the catheter wall, so that the thermistor extends outward approximately perpendicular to the direction of longitudinal extension (central axis) of the catheter. As before, the minimum amount of potting compound should be used to secure the thermistor, since this will also minimize the impact caused by the compound itself on the thermistor's ability to sense blood temperature. As before, one or more insulating lumens 900 may also be included in the catheter to isolate the thermistor from fluid-carrying lumen(s) 924.

Figure 10A:
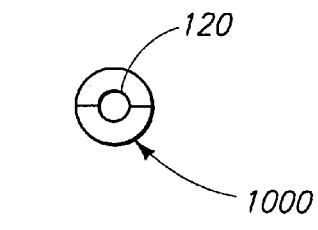
FIGS. 10a and 10b illustrate an embodiment of the invention in which the temperature sensor is mounted on an a separate insulating member that can be inserted along with the sensor into a catheter lumen.
Figure 10B:
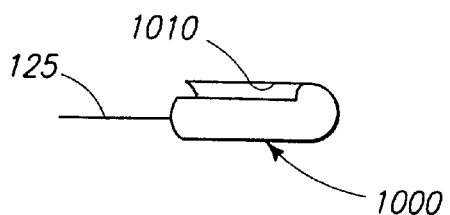

FIGS. 10*a* and 10*b* are a rear and an elevated side view, respectively, of an embodiment of the invention in which the thermistor 120 is mounted so as to lie within a recess in a separate insulating member 1000, which is shaped generally as a partially hollowed out cylinder with a closed, rounded, smooth leading surface and a slot 1010 into which the thermistor can be laid for mounting. The insulating member should be made of a smooth, thermally insulating material such as ceramic, metal, foam or Teflon. Polymers such as polyurethane may also be used, which would make it possible to injection-mold the member 1000. The insulator/thermistor sub-assembly is then inserted, for example, by pushing it in with a rod, into a suitable catheter lumen, such as the lumens 210, 310, 610 shown above for other embodiments of the invention. The slot should thereby be oriented, for example, using a key or similar tool, away from other catheter lumen(s) that carry thermal masses such as fluids and instruments.

Figure 11:
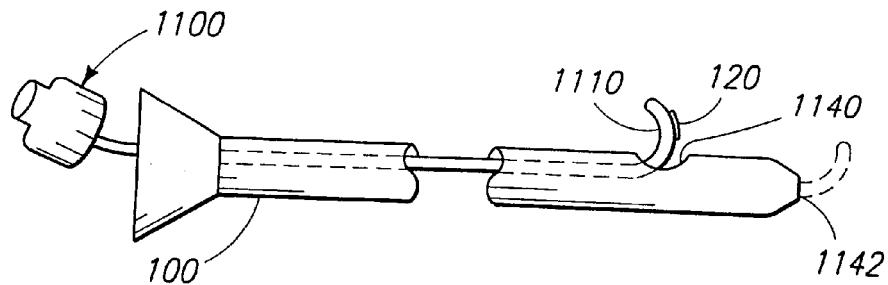
FIG. 11 illustrates an embodiment of the invention in which the temperature sensor is mounted on the tip of a probe that can be inserted into an access device such as a catheter.

In FIG. 11, an embodiment of the invention is shown in which the temperature sensor 120 is mounted on the tip 1110 of a separate device, for example, a guidewire or a probe 1100, which can be inserted into the access device 100. To deploy the sensor 120, once the access device is in place, the tip of the probe is inserted into a lumen of the device 100 and is then pushed in until the probe tip 1110 protrudes from a port 1140 that is either cut in the side wall of the catheter (as in some of the other embodiments described above), or is simply the innermost opening of the lumen in which the probe is inserted 1142. (Alternative exit of the tip of the probe is shown as a dashed line.) The probe thus itself acts as a structure that separates (and thus insulates) the temperature sensor from thermal masses. The tip of the probe is preferably curved to a mainly "J"-shape so that it will more easily extend through the port 1140 and away from the thermal influence of the parts of the access device; however, a straight tip is also acceptable. One advantage of this embodiment of the invention is that it could be inserted only if needed, in which case it can be sealed against blood leakage by a conventional hemostasis valve.

Figure 12A:
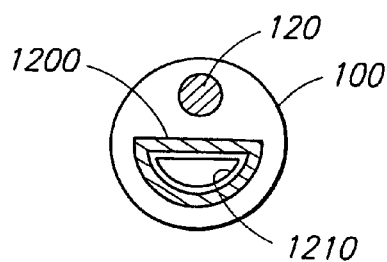
FIGS. 12a and 12b illustrate embodiments of the invention in which an insulating material is co-extruded with the catheter itself.
Figure 12B:
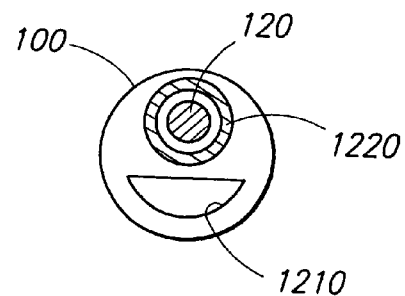

FIGS. 12*a* and 12*b* illustrate embodiments of the invention in which an insulating material is co-extruded with the catheter itself. In FIG. 12*a,* the insulating material 1200 is extruded along with the catheter 100 so as to surround an infusion (or instrument-carrying) lumen 1210 or, alternatively, at least a portion of it near the location of the temperature sensor. The insulating material, which may be of any known extrudable type then acts as a thermal barrier between the contents of the lumen 1210 and the temperature sensor 120. In FIG. 12*b,* the insulating material is co-extruded with the catheter so as to form a barrier layer 1220 that surrounds and thereby insulates the temperature sensor 120 itself.

Figure 13A:
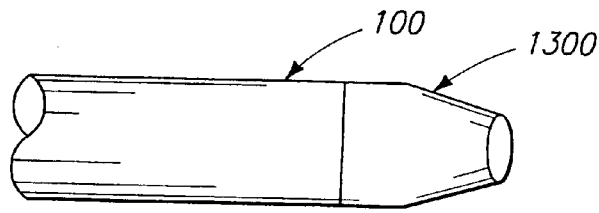
FIGS. 13a and 13b illustrate another embodiment of the invention, in which the temperature sensor is mounted within a catheter tip, that is initially formed as a member separate from the catheter body itself.
Figure 13B:
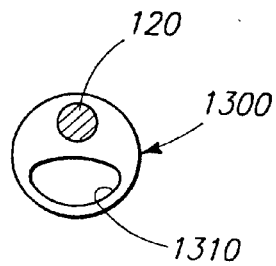

FIGS. 13*a* and 13*b* illustrate yet another embodiment of the invention, in which the temperature sensor 120 is mounted within a catheter tip 1300 that is initially formed as a member separate from the catheter body 100 itself, but is attached or bonded to the distal end of the catheter using, for example, a conventional adhesive. A lumen or through-hole 1310 is then formed in the tip 1300 to act as an extension of any appropriate and desired lumen within the main catheter body 100 to allow uninterrupted flow. The tip 1300 in this embodiment may then be made entirely of a highly insulative material. This completely avoids the need to extrude the insulating member over much or even the entire length of the catheter. It also makes possible the use of different materials in the insulating member and the main catheter body with no need for co-extrusion and without using more expensive material for the entire device.

Figure 14A:
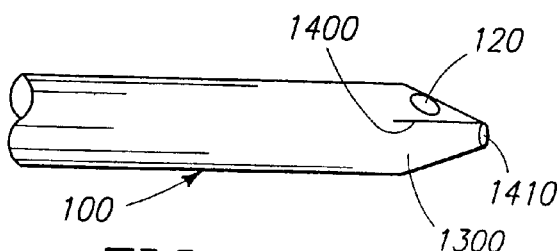
FIGS. 14a and 14b illustrate still another embodiment of the invention, in which the distal tip of the catheter splits after it is placed within the patient, with the temperature sensor and catheter lumen(s) containing thermal mass then deployed on either sides of the split.
Figure 14B:
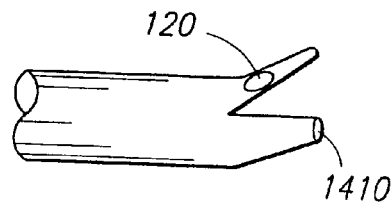

FIGS. 14*a* and 14*b* illustrate still another embodiment of the invention, in which the distal tip of the catheter 100 has a slit 1400. The temperature sensor 120 is mounted on or in the distal tip on one side of the slit, whereas the lumen(s) 1410 carrying the thermal mass extend through the tip on the other side of the slit. In short, in this embodiment, the distal tip of the catheter splits after the device is placed within a patient. Before insertion into the patient, the catheter tip 1300 is held together either mechanically, for example, with an internal catch that can be released using a wire that extends out of the proximal end of the catheter, or using an adhesive that dissolves when exposed to blood, or any other appropriate method. While in place, the slit 1400 opens to form an insulating gap (as shown in FIG. 14*b*) between the thermistor 120 and the thermal masses in the lumen(s) 1410.

Several different embodiments of the invention are described above. Common to all of the embodiments, however, is that they implement the method according to the invention by which the body temperature of a patient is sensed by a temperature sensor supported by an access device. As used here, the term "supported" means that the temperature sensor may be mounted on or within the access device; it may be permanently affixed to or within the access device; or it may be removably connected to or inserted into the access device. The term also includes any arrangement, as described for example in reference to FIG. 11, in which a temperature sensor is located on a separate device, which is inserted into and extended through the access device.

The access device is inserted into a patient, for example, into a vein, and at least one thermal mass is introduced into the access device. The temperature sensor is insulated thermally from the thermal mass. A signal wire is led from the temperature sensor to an external patient temperature monitor.

The invention also encompasses the method of manufacturing the access device. In most of the embodiments described above, this manufacturing method involves extruding the access device with a plurality of lumens—one lumen through which a temperature sensor is introduced and a signal wire is led (a sensor lumen), and at least one other lumen for carrying or guiding the thermal mass. The manufacturing method also includes the step of forming an insulating structure that thermally separates the temperature sensor from the thermal mass. The temperature sensor may be permanently or removably mounted at a distal end of the sensor lumen. The temperature sensor may be also mounted in a separate carrier which is placed in the sensor lumen. The manufacturing method may include some other or additional steps according to the embodiments described above, as will be understood by those skilled in the art.

Refer once again to FIG. 1. The output signal from a conventional temperature sensor such as the thermistor 120 has well-known characteristics. In general, the output signal is a voltage or current signal whose amplitude is functionally related to the temperature of the sensor. Moreover, the functional relationship between sensor temperature and the amplitude of the output signal may be linear, but seldom is. In fact, most temperature sensors are individually calibrated by the manufacturer, or require calibration by the user before actual use. However obtained, there is, though, a functional relationship.

Furthermore, in some cases, the temperature output signal may be compatible with input signals of existing patient monitors, but this is not always the case. As a simple example, amplification (scaling) and impedance matching (or impedance isolation) are often required to convert the output signal into a signal form and type that can be processed and displayed for the user.

According to the invention, the functional relationships a) between sensor temperature and the sensor output signal, on the one hand; and b) between output signal characteristics (such as impedance, amplitude range, and whether in the form of a voltage or current) are predetermined in any conventional manner (for example, through normal calibration or by accepting the manufacturer's calibration data). The signal conditioning necessary to implement the relationships is then implemented in the adapter 160. The conditioned signal is then applied to the monitor 170 for processing (if needed) and display.

In some cases, the only signal conditioning required is scaling. This can be done using a conventional resistive network, with the sensor output signal forming the input and the system output signal being taken from an appropriate point in the network. Conventional passive components may then be used to provide any necessary further conditioning such as impedance matching. This has the advantage of implementing the adapter 160 as a totally passive device. In other cases, conventional active components such as operational amplifiers with known resistive, capacitive and inductive feedback and feed-forward elements may be used to implement the signal conversion.

In many cases, the relationship between sensor output and temperature may be too irregular to implement accurately using purely passive or analog components. In these cases, the adapter may be implemented by including in the adapter 160 a Conventional analog-to-digital converter (ADC), a microprocessor, and a memory; note that a single conventional digital signal processor combines all these features in one component and may therefore in many applications be a suitable implementation. The relationship between the sensor output and temperature can then be implemented as a look-up table in memory, or as parameters of an approximating function. Using known methods, the microprocessor may then take as an input to the lookup table or approximating function the sensed and ADC-converted sensor output signal and generate the corresponding temperature signal, which, after any further conventional conditioning, is applied to the monitor 170.

In one embodiment of the invention that is particularly useful in a busy setting where only a quick and easy look at a patient's temperature is needed, the entire conditioning, processing and display circuitry 150 is included in a single hand-held unit. In this case, the power supply will typically be batteries and the monitor may be as simple as a conventional, low-power LCD display (along with conventional driving circuitry) showing temperature to, say, single decimal precision.

Using such a self-contained, handheld device, a nurse would connect the device to the temperature sensor by attaching the cable 190 to the connector 180, and the patient's temperature would then be displayed on the display 174 in a predetermined format. The connector 180 is preferably a conventional device such as a male/female plug pair that would allow the nurse to quickly connect and disconnect the device for readings from different patients. This would allow the nurse to take readings of many patients' temperatures quickly, with no need to wait for a conventional thermometer to stabilize, and with little discomfort to the patients themselves. Indeed, the nurse could take an already catheterized patient's temperature while he is asleep.

Assuming sufficiently powerful batteries, the self-contained embodiment of the system 150 could also include not only a memory, but also a simple input device such as a button connected to an internal electrical switch. Whenever the nurse presses the button, the instantaneous measured temperature is stored in the memory portion designated for a predetermined number of values for the patient. A time stamp of the measurement could also be generated using known techniques and stored along with each stored temperature measurement. By later recalling the stored values, for example by pressing the button according to some predetermined pattern, the nurse could then view the patient's recent temperature history. The software and hardware components needed to implement this one-button storage and recall system, even classified for several different patients, may be similar to those used, for example, in conventional electronic hand bearing compasses found on many well-equipped sailboats.

As an additional feature, the hand-held system could be provided with conventional circuitry enabling it to download its stored temperature information to another system such as a supervisory computer or patient monitor. The way in which such a feature is implemented is known. The way in which such temperature values, time-stamped or not, are stored for one or more patients and then recalled for viewing on a display is also well known.

Several different embodiments of the invention have been described above. It should be understood, however, that these are merely illustrative. The invention is not to be limited to the particular forms or methods disclosed; rather, the invention is to cover all modifications, equivalents and alternatives falling within the scope of the following claims.

What is claimed is:

1. A device for measuring the temperature of a temperature medium of a patient comprising:
   an access device that is insertable into the patient at a location of the temperature medium, including at least one thermal mass other than the temperature medium, such at least one thermal mass being located within a thermal lumen of the access device;
   a pair of ports formed in an outer wall of the access device;
   a temperature sensor supported by the access device;
   at least one insulating structure insulating the temperature sensor from the thermal mass; and
   a flow channel formed within the access device and extending between the pair of ports wherein the temperature medium occupies the flow channel, wherein the flow channel is located between the temperature sensor and the thermal lumen, the flow channel thereby both increasing thermal contact between the temperature sensor and the temperature medium and also thermally isolating the temperature sensor further from the thermal lumen.

2. A device as defined in claim 1, wherein the temperature sensor is located externally to an outer surface of the access device.

3. A device as defined in claim 1, wherein the temperature sensor is mounted in a carrier.

4. A device as defined in claim 3, in which the access device has more than one lumen, the insulating structure is formed as a barrier within the carrier and the carrier is held in one of the lumens of the access device with the barrier extending between the temperature sensor and the thermal lumen.

5. A device as defined in claim 4, in which the carrier is removably insertable in the lumen of the access device.

6. A device as defined in claim 3, in which the carrier is removably insertable in the lumen of the access device.

7. A device as defined in claim 1, in which each insulating structure extends between the temperature sensor and each thermal lumen.

8. A device as defined in claim 1, wherein the flow channel is located between the insulating structure and the thermal lumen.

9. A device as defined in claim 1, in which the temperature sensor is attached to the access device.

10. A device as defined in claim 1, wherein the insulating structure comprises at least one interior insulating lumen formed within the access device and extending between the temperature sensor and the thermal mass.

11. A device as defined in claim 1, wherein
the access device includes a plurality of lumens;
the temperature sensor is mounted within a recess in an insulating member; and
the insulating member, together with the temperature sensor, are mounted within one of the lumens of the access device so that the insulating member extends between the temperature sensor and the thermal lumen.

12. A device as defined in claim 1, wherein the insulating structure includes an insulating material co-extruded with the access device and surrounding at least a portion of each thermal lumen.

13. A device as defined in claim 1, wherein the insulating structure includes an insulating material co-extruded with the access device and surrounding the temperature sensor.

14. A device as defined in claim 1, wherein the insulating structure is expandable to increase the distance between the temperature sensor and the thermal mass.

15. A method for measuring the body temperature of a patient comprising the following steps:
supporting a temperature sensor on an access device;
inserting the access device into a blood vessel;
introducing at least one thermal mass into the access device; and
insulating the temperature sensor from the thermal mass by providing
a pair of ports formed in an outer wall of the access device; and
a flow channel formed within the access device and extending between the pair of ports, in which a temperature medium occupies the flow channel, wherein the flow channel is located between the temperature sensor and the thermal mass.

16. A method as defined in claim 15 further providing a signal conductor from the temperature sensor to an external patient temperature monitor.

17. A method as defined in claim 15, further including the following steps:
introducing the thermal mass via a thermal lumen located within the access device;
mounting the temperature sensor in a sensor lumen within the access device; and
forming at least one additional thermally insulating structure between the temperature sensor and the thermal lumen.

18. A method as defined in claim 15, further including the following steps:
forming an insulating structure as at least one insulating lumen within the access device; and
introducing a thermally insulating material into the insulating lumen.

19. A device for measuring the temperature of a temperature medium of a patient comprising:
an access device that is insertable into the patient at a location of the temperature medium, including at least one thermal mass other than the temperature medium, such at least one thermal mass being located within a thermal lumen of the access device;
a pair of ports formed in an outer wall of the access device;
a temperature sensor supported by the access device; and
an insulating structure insulating the temperature sensor from the thermal mass,
wherein the insulating structure comprises a flow channel formed within the access device and extending between the pair of ports so that the temperature medium occupies the flow channel, the flow channel is located between the temperature sensor and the thermal lumen, the flow channel thereby both increasing thermal contact between the temperature sensor and the temperature medium and also thermally isolating the temperature sensor further from the thermal lumen.

20. A device as defined in claim 19, wherein the flow channel is a chamber located near the temperature sensor.

21. A device as defined in claim 19, wherein the flow channel is a lumen passing through any portion of the length of the access device.

22. A device as defined in claim 19, wherein the temperature sensor is positioned within an indentation in an outer wall of the access device.

23. A device as defined in claim 19, wherein the insulating structure further comprises at least one interior insulating lumen formed within the access device and extending between the temperature sensor and the thermal mass.

24. A device as defined in claim 19, wherein the insulating structure further comprises an insulating material surrounding the temperature sensor.

25. A device for measuring the temperature of a temperature medium of a patient comprising:
an access device that is insertable into the patient at a location of the temperature medium, the access device having a plurality of lumens including at least one thermal lumen with a thermal mass other than the temperature medium;
a temperature sensor supported by the access device; and
at least one insulating gap extending near the location of the temperature sensor and between the temperature sensor and the plurality of lumens to thermally isolate the temperature sensor from the thermal mass.

26. A device as defined in claim 25, wherein the temperature sensor is located within a sensor lumen of the access device.

27. A device as defined in claim 25, in which:
the access device has an opening in an outer wall; and
the temperature sensor, when in a deployed position, extends into the opening, thereby increasing thermal contact between the temperature sensor and the temperature medium and further insulating the temperature sensor from the thermal mass.

28. A device as defined in claim 27, in which:

the temperature sensor is mounted on a carrier;

ends of the carrier are secured within the access device; and the carrier is positioned between the temperature sensor and each thermal lumen, thereby forming the insulating structure.

29. A device as defined in claim 27, in which the temperature sensor is a right-angle thermistor mounted to extend out of the opening mainly perpendicular to a central axis of the access device.

30. A device as defined in claim 27, wherein:

the temperature sensor is mounted within a carrier which protrudes as a loop out through the opening in the outer wall of the access device and ends of the carrier are secured within the access device;

the insulating gap comprises a flow channel for the temperature medium which is formed between the carrier and the access device at the position of the opening, and thus between the temperature sensor and the thermal mass; and the temperature sensor is exposed substantially over its entire outer circumference to the temperature medium, via only the carrier.

31. A device as defined in claim 25, in which the temperature sensor is adhesively attached and the adhesive is dissolvable at body temperature, the temperature sensor thereby increasing contact with the temperature medium when in position within the patient.

32. A device as defined in claim 25, wherein:

the access device has a lumen and a sensor port; and the temperature sensor is mounted on a distal tip of a probe which is insertable into the lumen of the access device so that the temperature sensor extends through the sensor port.

33. A device as defined in claim 25, wherein:

the insulating gap comprises a distal tip of the access device formed from an insulating material as a separate member; and the temperature sensor is mounted within the distal tip.

34. A device as defined in claim 25, in which:

the access device has a distal tip with a lengthwise extending slit;

the temperature sensor is mounted on a first side of the distal tip;

the plurality of lumens including at least one thermal lumen carrying the thermal mass extend through a second side of the distal tip; and the distal tip, once in a deployed position, is separated along the slit, with the first and second sides of the tip being located on either side of the slit.

35. A device as defined in claim 25, in which:

the access device is a central venous catheter;

the temperature medium is blood;

the thermal mass is an infusion fluid that is carried within one of the lumens; and the temperature sensor is a thermistor.

36. A device as defined in claim 25, wherein the temperature sensor is located within an indentation in an outer wall of the access device.

37. A device as defined in claim 25, wherein the temperature sensor is located externally to an outer surface of the access device.

38. A device as defined in claim 25, wherein the temperature sensor is mounted in a carrier.

39. A device as defined in claim 38, wherein the carrier is removably insertable in one of the lumens of the access device.

40. A device as defined in claim 38, wherein the insulating gap is formed as a barrier within the carrier.

41. A device as defined in claim 25, wherein the insulating gap comprises a generally elongated slit extending at least along a portion of the length of the access device.

42. A device as defined in claim 25, wherein the insulating gap is shaped to surround the temperature sensor.

43. A device as defined in claim 25, wherein the insulating gap is expandable.

44. A device as defined in claim 25, wherein the temperature sensor is mounted on the access device by a dissolvable potting compound.

\* \* \* \* \*